United States Patent [19]

Sisson et al.

[11] Patent Number: 4,586,505

[45] Date of Patent: May 6, 1986

[54] LARYNGEAL AND TRACHEAL STENT

[75] Inventors: George A. Sisson; Robert E. Berktold, both of Chicago, Ill.; Henry W. Lynch, Racine, Wis.

[73] Assignee: Universal Prosthetics, Inc., Racine, Wis.

[21] Appl. No.: 606,762

[22] Filed: May 3, 1984

[51] Int. Cl.$^4$ ............................................. A61B 17/00
[52] U.S. Cl. ..................................................... 128/344
[58] Field of Search .................. 128/344, 207.15, 342, 128/343; 604/96, 97, 98, 101, 104

[56] References Cited

U.S. PATENT DOCUMENTS

| | | | |
|---|---|---|---|
| 2,493,326 | 1/1950 | Trinder | 128/344 |
| 3,640,282 | 2/1972 | Kamen et al. | 128/344 |
| 4,417,576 | 11/1983 | Baran | 128/207.15 |
| 4,423,725 | 1/1984 | Baran et al. | 128/207.15 |

FOREIGN PATENT DOCUMENTS 2435183  4/1975  Fed. Rep. of Germany ...... 128/344

OTHER PUBLICATIONS

"Surgery of the Upper Respiratory System," William W. Montgomery (1973 Ed.), pp. 581 to 583 and 592 and 593.

Primary Examiner—Henry J. Recla
Attorney, Agent, or Firm—Quarles & Brady

[57] ABSTRACT

A laryngeal and tracheal stent which can be used to reconstruct the larynx or trachea consists of an elongated cylindrical stenting cuff with an independently inflatable retention cuff at the top and a second independent inflatable retention cuff at the bottom. The stent also has individual cuff pilot tubes for separately inflating or aspirating the stenting, top and bottom cuffs, and guide means for moving the stent into place.

4 Claims, 3 Drawing Figures

LARYNGEAL AND TRACHEAL STENT

FIELD OF THE INVENTION

The present invention relates to a surgical stent. More particularly, it relates to a stent for use in connection with the treatment of an injured larynx or trachea.

BACKGROUND OF THE INVENTION

The use of a solid molded silicone rubber stent for use in reconstructing a larynx is described by Dr. William W. Montgomery on pages 581 to 592 of his textbook "Surgery of the Upper Respiratory System" (1973 ed.). The stent is used to support tissue grafts and to block off flow through the trachea while the larynx is being reconstructed. The Montgomery stent which is relatively firm must be sutured in place. Therefore, its removal is quite traumatic.

There is a need for a laryngeal and/or tracheal stent which does not have to be sutured in place and which can be readily removed without trauma.

SUMMARY OF THE PRESENT INVENTION

The primary objects of the present invention are to disclose a new and unique laryngeal and tracheal stent which can be used to reconstruct the larynx or trachea.

It is a further object to disclose a laryngeal and tracheal stent which can be removed without traumatizing the surrounding tissues.

The stent of the present invention comprises a stenting cuff which is a cylindrical body of a soft medical application silicone rubber which is filled with an open celled foam, having a separate and distinct top or superior retention cuff at the top of the stenting cuff and a separate and distinct bottom or inferior retention cuff at the bottom of the stenting cuff. The retention cuffs when inflated are larger in external diameter than the stenting cuff. The stenting and retention cuffs are all fluidtight and each cuff has its own cuff pilot tube which can be used to either aspirate or inflate the cuff. The stent also includes guide means for guiding it into the proper position in the trachea. The guide means preferably comprises at least one string which extends from the top of the stent, through the stent and out the bottom of the stent. The string can also be useful to anchor the stent in place.

The stent is indicated for use in conditions which require that the trachea be separated temporarily from the tissue grafts used to reconstruct the larynx or trachea after "near total laryngectomy" or subtotal laryngectomy. Such conditions might be caused by cancer, injuries to the larynx and trachea or subglottic, glottic and/or supraglottic stenosis either iatrogenic or congenital.

In the preferred method of the present invention, the stent is inserted from below the larynx by passing the top guide string through the tracheotomy, into the trachea, pharynx and out the nose. Preferably the stent is initially introduced under general anesthesia, although in some instances it may be introduced under local anesthesia or as an office procedure. To facilitate introduction of the stent, the cuffs may first be aspirated to reduce the external diameter of the stent. The stent is guided into position by use of the guide strings. When the stent is properly positioned the retention cuffs are inflated and they retain the stent in place. The cuff pilot tubes and the guide strings may be used to anchor the stent in place. The stent may also be inserted via the mouth and pharynx from above the tracheotomy.

When it is desired to remove the stent the cuffs are aspirated or deflated. The stent may be removed and inserted by a physician or by the patient who has been given special training.

DESCRIPTION OF THE PREFERRED EMBODIMENT

Figure 1:
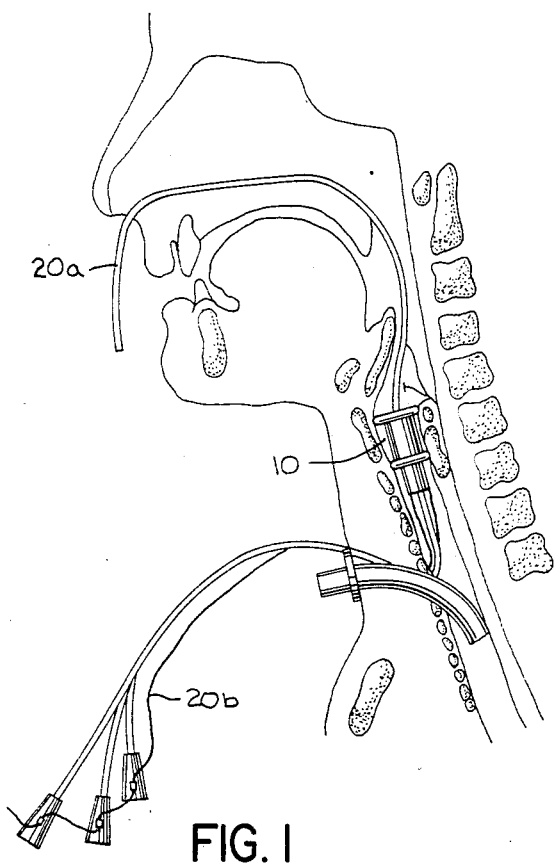
In FIG. 1 a schematic drawing showing the stent of the present invention properly positioned in a patient.
Figure 2:
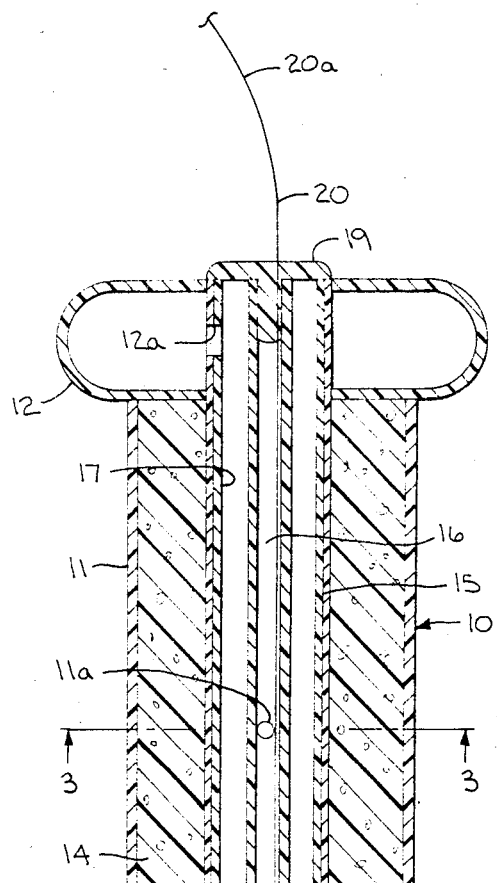
FIG. 2 is a longitudinal view, partly in section, of the preferred embodiment of the stent.
Figure 3:
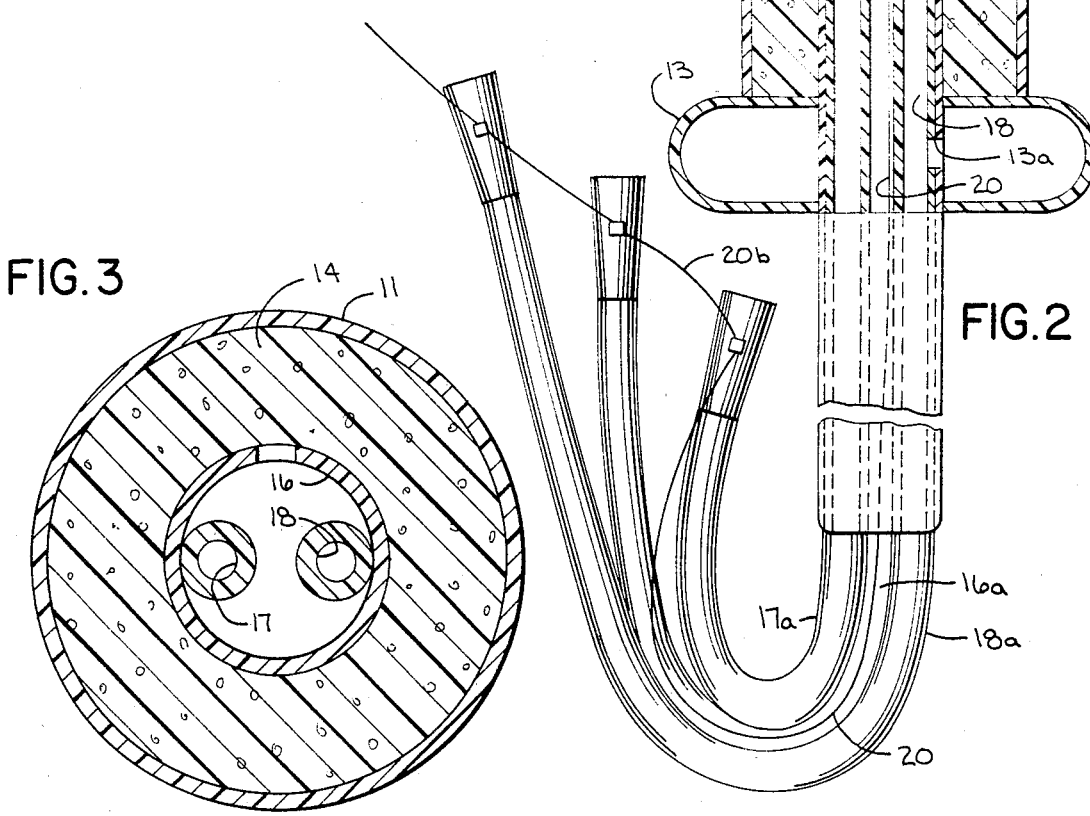
FIG. 3 is a view taken along lines 3—3 in FIG. 2.

In the preferred embodiment of the invention seen in FIGS. 1 to 3, the stent 10 includes a cylindrical stenting cuff 11, a top or superior cuff 12 and a bottom or inferior cuff 13. As seen in FIGS. 2 and 3 the stenting cuff 11 is filled with an open celled foam 14.

The stent, seen in FIGS. 2 and 3, includes a relatively large central tube 15 which has three separate and distinct lumens 16, 17 and 18 which run longitudinally the length of the tube 15. The top of the tube 15 and the upper ends of the lumens 16, 17 and 18 are all sealed by a plug 19. The other or lower ends of the lumens 16, 17 and 18 each communicate with its own separate and distinct cuff pilot tube 16a, 17a and 18a, respectively. Passageways 11a, 12a and 13a provide communication between the lumens 16, 17 and 18 and the interior of the fluidtight cuffs 11, 12 or 13, respectively.

As seen in FIGS. 1 and 2, a guide string 20 extends from the above top of the stent 10 through the lumen 16 of the tube 15 and out the bottom of the stent. The portion 20a of the guide string 20 which extends out of the top and the portion 20b which extends out the bottom of the stent 10 are used to guide the stent into proper position in the trachea. Portion 20b preferably is connected to the adapters of the cuff pilot tubes 16a, 17a and 18a to prevent them from tangling. As seen in FIGS. 1 and 2, the cuff pilot tubes 16a, 17a and 18a are of different lengths and staggered to reduce the bulk which must be drawn through the larynx.

The stent 10 is conveniently supplied in three sizes, small (12 mm diameter), medium (14 mm diameter) and large (16 mm diameter). The stent may be either inserted from above or below the larynx using the guide string 20. If the stent 10 is inserted from above the larynx, the bottom cuff 13 and the stenting cuff 11 are first aspirated and if the stent 10 is inserted from below the larynx, the top cuff 12 and the stenting cuff are first aspirated. With the use of the guide string 20, the stent is properly positioned in the larynx and then the remaining retention cuff is inflated.

As shown in FIG. 1, when the stent 10 is in place the top portion 20a of the guide string 20 extends out the patients nose and the bottom portion 20b extends out through a tracheotomy. The portions of the guide string 20 extending outside the body may be used to anchor the stent 10 in place.

In the preferred practice of the invention, once stent 10 is in place the top and bottom cuffs 12 and 13 are inflated with saline. The stenting cuff 11 is not inflated but is allowed to assume its normal shape at ambient pressure. The position of the stent may be verified endoscopically at the conclusion of the procedure.

If a patient is thoroughly instructed in the care and maintenance of the stent, he can remove and, if necessary, replace the stent himself. A patient familiar with the mechanics of the device can pull the stent up into his mouth if it becomes dislodged until a physician can be contacted.

The stent is not designed for pediatric use and should not be inserted into a larynx which is too small. It is also not to be used where allergic reaction to the material of the stent may be a complication.

The stent of the present invention may be used in the same manner as the Montgomery stent to support graft tissue for reconstruction of the larynx. However, when the stent of the present invention is used, it is not necessary to suture the graft to the stent because the graft will be adequately maintained in position by the cooperation of the stenting cuff 11, and the sides 12a and 13a of the top and the bottom retention cuffs 12 and 13, respectively.

Although the preferred material for the components of the stent, other than the string, is medical grade silicone rubber, any other suitable biocompatable material may be used provided it functions in a similar manner. The strings are preferably of Dacron or a similar biocompatable material.

It will be apparent of those skilled in the art that a number of changes and modifications may be made in the described stent without departing from the spirit and scope of the invention. For example, although in the preferred embodiment both of the retention cuffs have been described as inflatable another embodiment of the invention in which the upper retention cuff is filled with foam can be used, if desired. Therefore, it is intended that the invention not be limited except by the claims which follow.

We claim:

1. A laryngeal or trachael stent consisting essentially of a hollow cylindrical body of soft medical application material having a central bore, said body having a first inflatable retention cuff about the outer periphery of one end and a second inflatable retention cuff about the outer periphery of the other end, each of said cuffs being fluid tight and having its own pilot tube for adding or subtracting fluid, each pilot tube having a proximal end extending exterior to said hollow cylindrical body and a distal end which extends through the central bore of said body and communicates with the interior of each respective cuff, said stent further including externally extending guide means for guiding the stent into proper position in a larynx or trachea, said guide means comprises at least one string which extends through and externally out of both ends of the central bore, said string being secured to said hollow cylindrical body, and means associated with said central bore for blocking fluid flow therethrough.

2. A stent of claim 1 in which the hollow cylindrical body includes a fluid tight cylindrical chamber which surrounds the central bore and which is provided with its own pilot tube for adding or subtracting fluid to said chamber.

3. A stent of claim 2 in which the cylindrical chamber is filled with an open-celled foam.

4. A method of inserting a stent comprising a hollow cylindrical body having an inflatable retention cuff at each end and means for blocking flow through said hollow body, guide means secured to said body and extending from each end of the body, said method comprises performing a tracheotomy, inserting one end of the guide means into the trachea through the tracheotomy, guiding the stent through the tracheotomy into the trachea to a proper position above the tracheotomy by use of the guide means and then inflating at least one of the inflatable retention cuffs to secure the stent in position closing off the trachea.

* * * * *